United States Patent [19]

Kawaguchi

[11] 4,243,386
[45] Jan. 6, 1981

[54] ORTHODONTIC APPLIANCE

[75] Inventor: Kozo Kawaguchi, Ohkuma, Japan

[73] Assignee: GAC International, Inc., Commack, N.Y.

[21] Appl. No.: 887,062

[22] Filed: Mar. 16, 1978

[51] Int. Cl.³ .............................................. A61C 7/00
[52] U.S. Cl. ...................................................... 433/9
[58] Field of Search ................... 32/14 A; 248/205 A, 248/206 R; 433/9

[56] References Cited

U.S. PATENT DOCUMENTS

| 3,745,653 | 7/1973 | Cohl | 32/14 A |
|---|---|---|---|
| 3,932,940 | 1/1976 | Andren | 32/14 A |
| 4,068,379 | 1/1978 | Miller et al. | 32/14 A |
| 4,100,678 | 7/1978 | Yatabe | 32/14 A |

*Primary Examiner*—Gene Mancene
*Assistant Examiner*—Michael J. Foycik, Jr.
*Attorney, Agent, or Firm*—Kenyon & Kenyon

[57] ABSTRACT

An orthodontic appliance is disclosed which is suitable for supporting a wire during treatment. The appliance is adapted to be directly adhered to the surface of the patient's tooth and includes on the base thereof a plurality of indentations which have the surfaces thereof roughened so as to provide a mechanical lock with the adhesive and facilitate direct adherence of the appliance to the tooth's surface with a superior bonding action.

10 Claims, 2 Drawing Figures

ORTHODONTIC APPLIANCE

BACKGROUND OF THE INVENTION

This invention is directed generally to an orthodontic appliance, and more particularly, to one which is adapted to be adhered directly to the surface of a tooth.

In recent years, advances have been made in direct adhering orthodontic brackets for replacement of the prior art cumbersome and less desirable bands. Generally speaking, direct adhering orthodontic brackets which provide a satisfactory bond so as to enable the necessary treatment to be rendered, come in two forms. One form of bracket requires a hole penetrating the entire thickness of the base from the front to the back surface, i.e., from the contact surface to the exposed surface. These holes allow the cement to flow from the dental surface to the front surface of the base member and over the edges, thus forming the locks which hold the base member and connecting brackets to the dental surface.

Other base members are provided in the form of a wire mesh wherein the adhesive flows through the holes in the wine mesh and forms a locking bond which adheres the orthodontic appliance to the patient's tooth. A variation of the above wire mesh system is a two section base member which consists of a hard metal sheet welded over a wire screen material, the assembly of which is welded to the bracket.

Certain disadvantages are however, present even with these more advanced systems. For instance, in these systems the base member must provide a maximum surface area which makes the appliance highly conspicuous and thus esthetically unpleasing. Moreover, certain problems arise in attempting to adhere such a member to smaller size teeth or partially erupted teeth. With these prior art systems, the orthodontist must be careful to insure that he has placed a sufficient amount of cement on the bracket so that it overflows and forms a locking relation. Failure to do so will result in a poor bond. Also, with these prior art appliances excess cement, if allowed to remain, forms food traps. In practice, the cement is feathered; this procedure must be performed carefully or else the cement will be excessively removed and the bond weakened. On the other hand, if excessive cement remains on the exposed surface of the base member, it may lock the tie wing areas of the bracket or interfere with the arch wires. It has also been found in practice that the cement exposed on the base member surface tends to darken with age. Some of this darkening is due to normal aging, some due to staining from food, tobacco, coffee and other liquids. Also, plaque and fungus like growth has sometimes been found growing on the surface of the exposed cement. Moreover, the irregular nature of the exposed cement acts as a food trap and so contributes to the formation of caries.

By the means disclosed herein, an orthodontic appliance is provided which may be directly adhered to the surface of a tooth and which has superior bonding without the above disadvantages encountered in the prior art systems.

SUMMARY OF THE INVENTION

Briefly stated, the invention disclosed herein provides an orthodontic appliance which is adapted to be adhered directly to the surface of a patient's tooth. The appliance includes an orthodontic bracket suitable for supporting a wire and a base member which connected to the lower portion thereof. The base member, attached to the bottom of the bracket, forms a flange which extends from the lower portion of the bracket. On the contact or rear surface of the base member (the surface engaging the tooth) there is provided a plurality of indentations which extend into the thickness of the base member but which do not protrude through the base member onto the exposed surface thereof. These indentations include a roughened surface which is sufficient to facilitate a locking relationship with an adhesive and thus enables the appliance to be directly adhered to the surface of the tooth.

These indentations may be in the form of holes which preferably cover approximately 75% of the area of the rear surface of the base member. Other geometric shapes such as squares, triangles, rectangles, stars and the like may also be used. Similarly the indentations may be in the form of lines either straight or irregularly shaped. Regardless of the shape, the indentations extend into the thickness of the base member approximately two thirds but as mentioned do not protrude through the base member onto the exposed surface. In other words, when the indentations are circular they in effect constitute blind holes. At least the walls of the indentations are provided with a roughened surface to obtain a locking relation with the adhesive which thus enables the appliance to be directly adhered to the tooth's surface. This roughened surface, which may be provided over the entire rear surface of the base member, preferably has a finish of approximately 6 to 10 microns in depth and with a spacing between the irregularities of approximately 5 to 13 microns.

The base member is made from stainless steel material and is approximately 0.012 inches thick. The indentations, when in the form of spaced blind holes, are preferably of a diameter of 0.012 inches and extend into the base member for approximately a depth of 0.008 inches. The center to center spacing of the holes is preferably 0.020 inches.

In another embodiment the orthodontic applicance is provided in the form of a bracket, again which is adapted to be adhered directly to the surface of the tooth. The bracket has an upper portion suitable for supporting a wire and a lower portion which terminates in a base or tooth engaging surface. This surface generally conforms to the surface to which it is applied and has therein a plurality of indentations which extend into the base portion of the bracket. These indentations again include a sufficiently roughened surface which facilitates a locking relationship with an adhesive so as to enable the bracket to be directly adhered to the surface of the tooth. Also, other features discussed previously may be incorporated into this embodiment.

It is accordingly, an object of this invention to provide an improved orthodontic appliance which may be directly adhered to the surface of the tooth.

It is also an object of this invention to provide an orthodontic appliance which is suitable to be directly adhered to the surface of the tooth without any adhesive overflow either on the side or front of the appliance.

It is a further object of this invention to provide an orthodontic appliance of a one piece construction which is suitable to be adhered to the surface of the tooth and which has a base smaller than those conventionally provided while yet providing an adequate bond between the appliance and the tooth.

These and other objects, advantages and features of the invention will become more apparent from the following description taken in conjunction with the accompanying drawings.

DESCRIPTION OF THE PREFERRED EMBODIMENT

Figure 1:
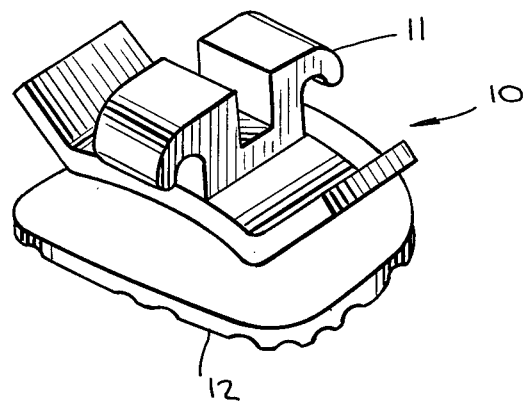
FIG. 1 is a perspective view of the base member and orthodontic bracket attached thereto.
Figure 2:
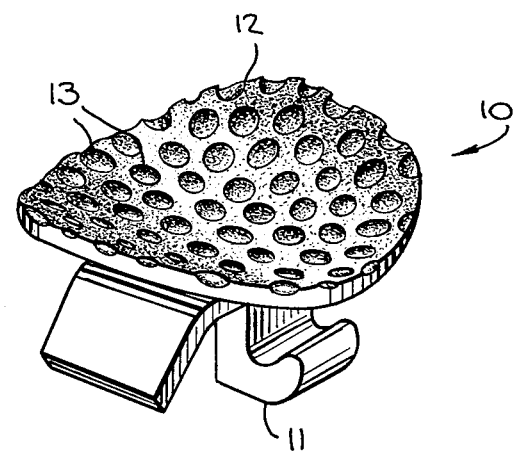
FIG. 2 is a perspective view of the rear or tooth engaging surface of the base member of this invention.

The orthodontic appliance of this invention, indicated generally at 10, includes a bracket 11 and a base member 12. Into the base member 12 are positioned a number of indentations which in the illustrated embodiment are in the form of blind holes 13. The base member consists of a stainless steel sheet material which is approximately 0.012 inches in thickness and is generally sized and shaped to conform to the morphology of the tooth. The front, or exposed surface is smooth and of a matte finish as illustrated in FIG. 1. Onto the front is welded one of the numerous types of orthodontic appliances conventionally employed.

The blind holes 13 in the rear or tooth contacting surface are a series of blind holes 0.012 inches in diameter and centered 0.020 inches apart. The holes penetrate into the base member approximately 0.008 to 0.009 inches deep but do not protrude onto the exposed surface. The entire rear or contact surface of the base member 12, including surfaces of the blind holes 13, have a roughened finish. Specifically, the walls and bottom of each of the blind holes 13 are in the form of a roughened surface. This roughened surface has a finish of 6 to 10 microns in depth and a distance between irregularities of 5.5 to 13 microns. The roughened surfaces, particularly those on the side walls of the holes, when filled with a bonding cement, forms an undercut which bonds the bracket to the body of the cement and the dental surface.

The appliance of this invention has been found to have a significantly greater holding power than those of the prior art both in tensile and in shear tests. This has many advantages, including the fact that the base size can be reduced making the entire appliance less conspicuous and thus more esthetically appealing. Also, the clinician need not be concerned with excessive overflowing of the cement onto the front surface of the base member which as previously discussed has a number of undesirable effects.

It is believed that the greater the depth of the blind hole 13, the greater the holding power since the total side area (length times depth of the side walls) determines the total strength of the bond. In the case when a base member of 0.012 inches is employed, the maximum practical depth is 0.009 inches. Any greater depth would thin out the bottom of the hole so that it might break out and allow the cement to flow over the exposed surface of the base member. It has also been found that the material for the base member must be sufficiently hard. Too soft a material tends to give and thus breaks the bond. One suitable material is 304 stainless steel.

In the preferred manner of fabricating the orthodontic appliance of this invention, the base member is first photo-etched by conventional means to form the blind holes 13 in the flat sheet which serves as the base member 12. The photo-etched surface is then sand blasted to roughen it. It has been found that a sharp piramidal abrasive gives the best holding strength. After etching, the material is treated in a 40°-50° Be(Baume) $FeCl_26$-$H_2O$ acid which gives fine sharp edges to the surface. The thus treated base members are then formed in the usual manner and welded to the bracket. The welding is accomplished however in a non oxidizing atmosphere to avoid surface burning since no tumbling can be done after welding. Tumbling would remove the roughness of the base member. Other fabricating methods, such as possibly the lost wax or investment casting process, may also be utilized in forming the orthodontic appliance of this invention.

Because of the superior bond achieved with a smaller base member, a one piece bracket may be employed. Such a bracket has on the upper end thereof a conventional bracket portion while the lower end forms the base member. The lower portion is generally conformed to the surface of the patient's tooth and is provided with photo etched indentations as previously discussed. Also the bottom surface is roughened in order to provide for better adherence.

Several clinical tests and evaluations have been made which demonstrate that the base and bracket of this invention provide superior bonds to that achievable with the prior art devices. More specifically, it has been found that the base member of this invention, using the same type of an adhesive, had a bond strength of 135 kg per square centimeter versus 110 kg per square centimeter for a foil-mesh commercial type base member, i.e. a two section construction of mesh and sheet material. Moreover, when compared to perforated base members, it has been found that using the same type of adhesive on a peripherally perforated bracket produced a bond strength of 62 kg per square centimeter while for a multi perforated base member (one with perforations throughout) the strength was 68 kg per square centimeter whereas the bracket of this invention had a bond strength of 163 kg per square centimeter.

On the basis of these test results, it can be readily seen that a superior bond is achieved utilizing the base member formed in accordance with this invention. Also because the base member does not require a large area in order to provide an adequate bond, a one piece bracket may be employed when formed with a base surface as herein described.

It is recognized that altough the above description is directed to a preferred embodiment of the invention, it is noted that other variations and modifications will be apparent to those skilled in the art and, therefore, may be made without departing from the spirit and scope of the present disclosure.

What is claimed is:

1. An orthodontic appliance adapted to be adhered directly to the surface of a tooth which comprises an orthodontic bracket suitable for supporting a wire, and a base member connected to the lower portion of said orthodontic bracket and forming a flange extending from said lower portion of said bracket, said base member having in the rear surface thereof a plurality of indentations which extend into the thickness of said base member but do not protrude onto the other surface thereof, said indentations including a sufficiently roughened surface to facilitate a locking relation with an adhesive so as to enable said appliance to be directly adhered to the surface of said tooth, said roughened surface having a finish of approximately 6 to 10 microns in depth with a spacing between irregularities of approximately 5 to 13 microns.

2. An orthodontic appliance as defined in claim 1 wherein said indentations are in the form of photo etched spaced holes disposed over the rear surface of said base member.

3. An orthodontic appliance as defined in claim 2 wherein said holes cover approximately seventy-five percent of said rear surface of said base member.

4. An orthodontic appliance as defined in claim 1 wherein said indentations extend into said base member approximately two-thirds of the thickness of said base member and have on at least the walls thereof a roughened surface to facilitate a locking relation with an adhesive thus enabling said appliance to be directly adhered to the surface of said tooth.

5. An orthodontic appliance as defined in claim 1 wherein said base member is approximately 0.012 inch thick stainless steel and said indentations are in the form of spaced 0.012 inch diameter holes extending into said base member for a depth of approximately 0.008 inches.

6. An orthodontic bracket adapted to be adhered directly to the surface of a tooth which comprises an upper portion suitable for supporting a wire and a lower portion which terminates in a base portion which is generally conformed to the surface of the tooth to which it is to be applied, said conformed surface of said base having a plurality of indentations which extend into the base portion of said bracket, said indentations including a sufficiently roughened surface to facilitate a locking relation with an adhesive so as to enable said bracket to be directly adhered to the surface of said tooth, said roughened surface having a finish of approximately 6 to 10 microns in depth with a spacing between irregularities of approximately 5 to 13 microns.

7. An orthodontic bracket as defined in claim 6 wherein said indentations are in the form of photo etched spaced holes disposed over the conformed surface of said base.

8. An orthodontic bracket as defined in claim 7 wherein said holes cover approximately seventy-five percent of said conformed surface of said base.

9. An orthodontic bracket as defined in claim 6 wherein said indentations extend into said base portion a distance of at least 0.008 inches and have on at least the walls thereof a roughened surface to facilitate a locking relation with an adhesive thus enabling said bracket to be directly adhered to the surface of said tooth.

10. An orthodontic bracket as defined in claim 6 wherein said indentations are in the form of spaced 0.012 inch diameter holes extending into said base portion for a depth of approximately 0.008 inches and which are spaced from one another on approximately 0.020 inch centers.

* * * * *